United States Patent
Hartmann et al.

(10) Patent No.: US 6,539,285 B1
(45) Date of Patent: Mar. 25, 2003

(54) METHOD AND APPARATUS FOR PROCESS CONTROL USING FOURIER TRANSFORM INFRARED SPECTROSCOPY

(75) Inventors: Wilfried Hartmann, Halle/Saale (DE); Arno Simon, Karlsruhe (DE)

(73) Assignee: Bruker Optik GmbH, Ettlingen (DE)

( * ) Notice: Subject to any disclaimer, the term of this patent is extended or adjusted under 35 U.S.C. 154(b) by 210 days.

(21) Appl. No.: 09/636,560

(22) Filed: Aug. 11, 2000

(51) Int. Cl.[7] ............................................. G05B 21/00
(52) U.S. Cl. ........................ 700/266; 702/22; 702/23; 702/25; 422/62; 436/164
(58) Field of Search ................... 700/266; 250/341.2, 250/339.07, 339.08, 339.09; 702/23, 25, 22; 422/62; 356/436, 73, 300; 436/164

(56) References Cited

U.S. PATENT DOCUMENTS

| | | | |
|---|---|---|---|
| 5,051,551 A | * 9/1991 | Doyle | 250/341.2 |
| 5,185,640 A | * 2/1993 | Wilks, Jr. et al. | 356/300 |
| 5,262,961 A | * 11/1993 | Farone | 702/23 |
| 5,418,615 A | * 5/1995 | Doyle | 356/436 |
| 5,566,086 A | * 10/1996 | Doyle | 702/25 |
| 5,763,883 A | * 6/1998 | Descales et al. | 250/339.09 |
| 5,807,750 A | * 9/1998 | Baum et al. | 436/164 |
| 5,893,046 A | * 4/1999 | Wu et al. | 702/22 |
| 6,118,520 A | * 9/2000 | Harner | 356/73 |
| 6,137,108 A | * 10/2000 | DeThomas et al. | 250/339.07 |
| 6,284,196 B1 | * 9/2001 | Casal et al. | 422/62 |

* cited by examiner

Primary Examiner—Jill Warden
Assistant Examiner—Brian Sines
(74) Attorney, Agent, or Firm—Paul Vincent

(57) ABSTRACT

The invention concerns a method and a device for process control of reaction processes using Fourier transform infrared spectroscopy. In accordance with the invention, an interferogram is generated before or after interaction with the compositions. Subsequent thereto, the interferogram is inspected in segments for externally introduced intensity fluctuations. The intensity fluctuations are subjected to an analysis procedure involving integration, differentiation, or the like, and on the basis of this evaluation, a decision is made as to whether or not the interferogram has an acceptable degree of interfering signals. The interferogram is labeled with this evaluation result and the procedure is repeated a plurality of times. After a sufficient number of acceptable interferograms have been collected, the acceptable interferograms are summed and subjected to a Fourier transform process to extract the frequency dependence. In this manner, Fourier transformation infrared spectroscopy techniques can be applied for process control of processes which would otherwise be impossible due to unacceptably large degrees of interference caused primarily by bubble formation.

14 Claims, 4 Drawing Sheets

METHOD AND APPARATUS FOR PROCESS CONTROL USING FOURIER TRANSFORM INFRARED SPECTROSCOPY

BACKGROUND OF THE INVENTION

The invention concerns a method and a device for process control using Fourier transform (FT) infrared (IR) spectroscopy in which various substances are fed into a storage vessel and stirred.

Measurements in FT IR spectroscopy assume and require that the IR radiation being analyzed is static (constant in time) during the period of time during which the measurement is carried out. An interferogram is generated typically by driving a mirror in a forward and backward direction at substantially constant velocity to generate an intensity versus mirror position or path exhibiting a so-called central burst containing the spectral information. A plurality of measurements are normally carried out and added together to improve signal to noise ratio. This procedure requires a fixed phase relationship between the interferograms which are added together. Subsequent to addition, the spectrum is extracted via Fourier transformation.

Application of this procedure to analytic measurements is not possible if there are time dependent, dynamic changes in the interferogram caused by disruption of the measurement system (the sample, the detector, the electronics, etc.) during the measurement time. In applications involving chemical production processes, liquids and gases are added to a production vessel, are generated during the production process, and/or are stirred and mixed. Such processes require periodic changes in system parameters such as temperature, the gas additive constituents, the liquid additives etc. Dynamic feedback control and regulation of such systems is required in order to check whether or not acceptable conditions have been established prior to carrying out the next step.

Use of Fourier transform infrared spectroscopy for chemical process control is difficult, since the stirring and mixing processes cause changes in the physical properties of the sample during the measurement. These dynamic processes are associated with random disturbances of various character which cause major disruptions in the recorded interferogram which distorts the subsequently Fourier transformed spectrum. These distortions can be of such a substantial magnitude as to preclude analysis of the chemical composition of the reactants using Fourier transform IR spectroscopy.

In view of these problems, it is the underlying purpose of the invention to provide a method and an apparatus which is capable of recognizing and compensating for dynamic disturbances in process controlled chemical processes such that analysis using Fourier transform infrared spectroscopy is possible.

SUMMARY OF THE INVENTION

This purpose is achieved in accordance with the invention by passing a beam of infrared radiation through a chemical composition, generating an interferogram of the infrared radiation, analyzing regions of the interferogram for intensity fluctuations, labeling the interferogram as being acceptable or non-acceptable in dependence on the analyzed intensity fluctuations and adding together the acceptable interferograms to form a sum interferogram, prior to Fourier transformation.

In accordance with the invention, it has been discovered that the major source of disturbance for IR FT applications in such chemical processing control methods is caused by the formation of bubbles passing through the liquid samples. These bubbles result in widely varied disturbances in the measured interferograms in dependence on the size, speed and direction of travel of the bubbles through the measuring region. Studies of bubble formation in these chemical processes have led to the realization that the bubbles have a characteristic frequency, time and amplitude dependence in the interferograms. Through inspection of the portions of the interferograms specific measurements can be analyzed and selected, wherein interferograms containing substantial bubble interferences can be reliably eliminated from the spectrum. The inspected regions can be integrated, differentiated or be subjected to various other mathematical operations.

In a preferred embodiment of the invention, the selection process for acceptable interferograms comprises analysis of either the amplitude, the time, and/or the frequency dependence of the intensity fluctuations. This embodiment has the advantage that a characteristic signature of bubble formation in the measurement can be analyzed and extracted in order to determine which interferograms can be included in the sum spectrum and which must be discarded.

In an improvement of this embodiment, the intensity of fluctuations within an analyzed region are added together to generate a sum value. This improvement has the advantage of reducing investigation of disturbances contained in the interferogram to one single parameter. After establishment of an acceptable value for this parameter, the parameter can be used as a signature for acceptable and non-acceptable interferograms.

In a preferred application of this improvement, the sum value is compared to a maximum allowed value. This aspect of the invention involves realization that the intensity changes in the non-spectral region of the interferogram are subject to fluctuations about a mean value in both positive and negative directions. Analysis of the maximum possible positive excursion of the sum value has shown, in accordance with the invention, that a single parameter can be extracted from the interferogram characteristic of acceptable and unacceptable levels of bubble formation.

In another aspect of this improvement, the sum value is compared to a maximum possible negative value. This aspect takes into consideration the fact that the average positive and negative excursions of the intensity fluctuations from a zero value do not, in general, average out to precisely zero over a region investigated. It has turned out that the degree of deviation of the average value from a zero value is a measure of the degree of disturbance in a given measurement. This parameter is a suitable one for selecting acceptable and non-acceptable interferograms.

In an improved embodiment, standard commercially available spectroscopy software procedures are used to select acceptable interferograms. This embodiment has the advantage that the user does not have to write his own software algorithms in order to analyze regions of the interferogram in order to decide whether or not a given interferogram should be selected. Instead, standard analysis programs available to the user, e.g. for summing regions of spectra, for analyzing the frequency dependence of regions of spectra etc., can be utilized to generate the criteria for acceptable interferograms.

The invention is also directed to a device for process control of chemical processes using Fourier transform infrared spectroscopy. The device involves means for feeding compositions into a reaction vessel and means for stirring the composition. In accordance with the invention, means are provided for passing a beam of infrared radiation through the composition and for measuring an interferogram of infrared radiation which has passed through the composition. Analysis means are provided for inspecting regions of the interferogram for intensity fluctuations. Means are provided for labeling interferograms having fluctuation disturbances below and/or above a certain level, wherein spectra are added together to form a sum interferogram comprising only those spectra selected for acceptable interference levels.

Various embodiments of this device provide means for carrying out the various method steps discussed above and will not be described in further detail here.

Further aspects of the invention are delineated below in a preferred embodiment with reference to the drawings. The particular features disclosed in the drawing and in the specification as well as the claims can be important to the invention individually or collectively in arbitrary combination. The embodiment is not an exhaustive enumeration of inventive configurations rather has exemplary character only for illustration of the invention and its best mode.

DESCRIPTION OF THE PREFERRED EMBODIMENT

Figure 1:
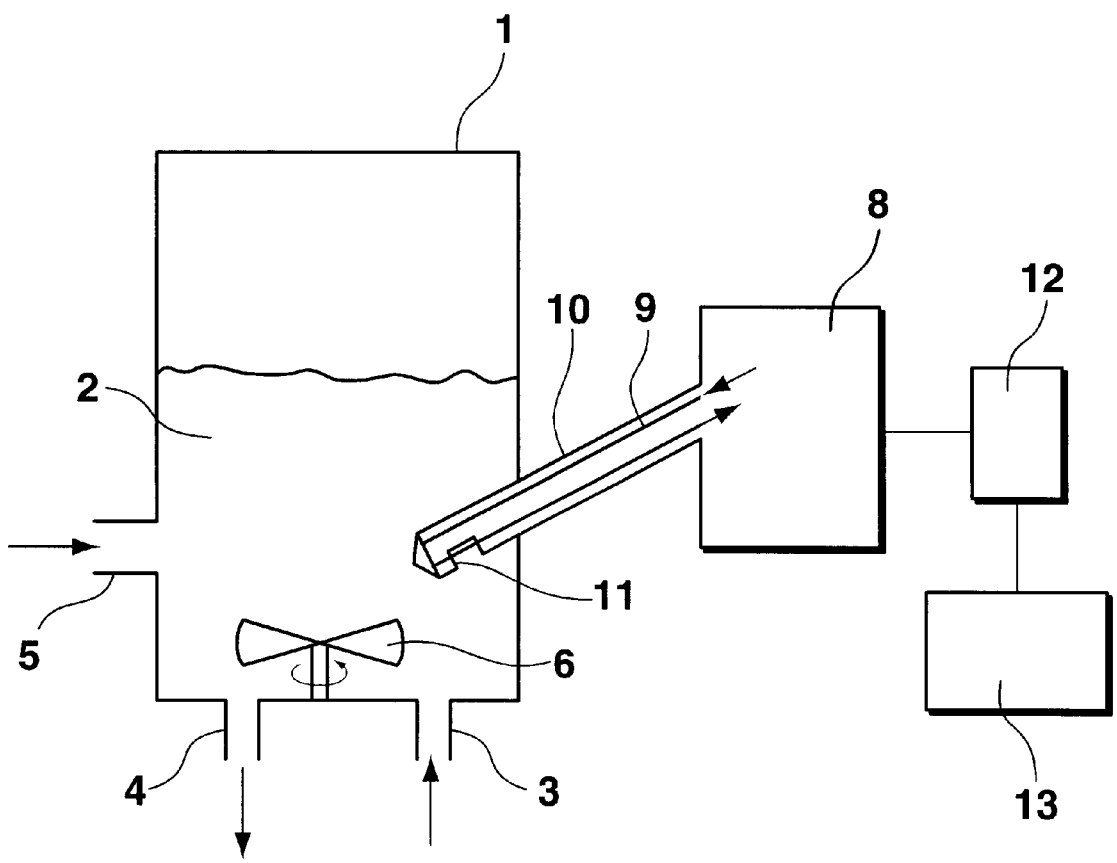
FIG. 1 shows an over-all schematic view of an apparatus suitable for carrying out the method in accordance with the invention.

FIG. 1 shows a schematic view of the apparatus in accordance with the invention. A container 1 contains a composition 2. A liquid inlet 3 is provided for introducing the composition 2 into the container 1. A liquid outlet 4 permits draining of the composition 2 from the container 1. A gas inlet 5 is provided for introduction of gaseous substances into the composition mixture. A stirring member 6 is located at an appropriate position within the composition container 1 for stirring the composition 2 and gas from the gas inlet 5.

In interferometer means 8 generates an infrared radiation beam 9 which is passed via a probe 10 from the interferometer means 8 into the composition container 1. The probe 10 has a gap 11 through which the infrared beam 9 passes for interaction with the liquid in the composition 2 within the composition container 1. Following interaction, the beam 9 passes back into the interferometer means 8. For Fourier transform measurements, the interferometer means 8 comprises a moveable mirror whose velocity is substantially constant during the period of time when the data of the interferogram, containing the spectral information, is recorded. The nature and composition of the interferometer means are well known to those of average skill in the art and further discussion thereof is therefore unnecessary.

Intensity signals corresponding to the interferogram pass from the interferometer means 8 to an interferogram analyzer 12. The interferogram analyzer 12 can comprise hardware or software used in standard electronic data processing systems such as computers. The interferogram analyzer 12 analyzes portions of the interferogram for unacceptable fluctuations which would otherwise prevent analysis of the interferogram into a Fourier transformed spectrum. Individual interferograms are labeled by the interferogram analyzer 12 and used in subsequent analysis via a Fourier transform device 13 acting on a summed interferogram to generate the spectrum of the chemical composition 2 under investigation.

Figure 2:
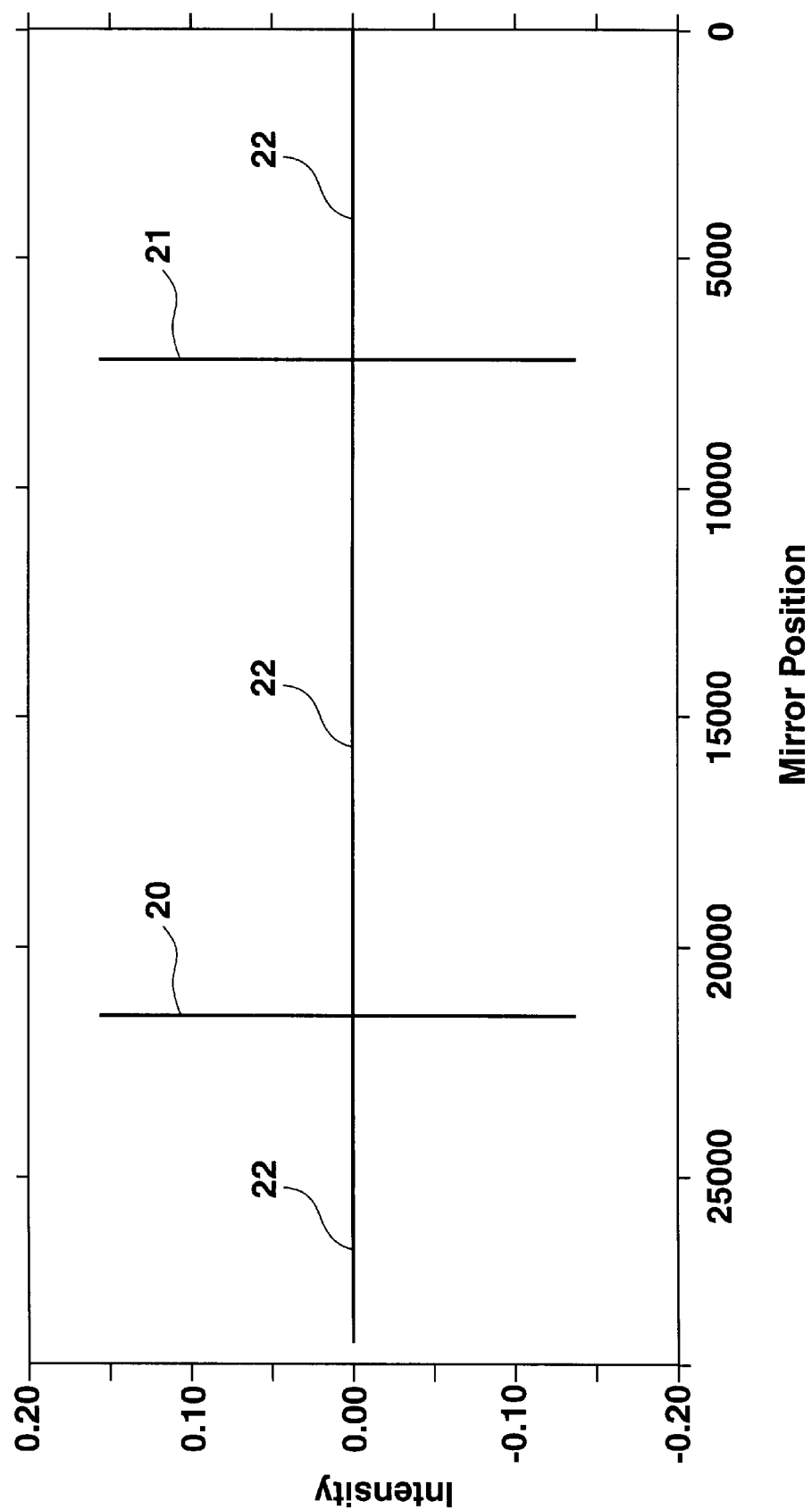
FIG. 2 shows an interferogram having a low level of interference.
Figure 3:
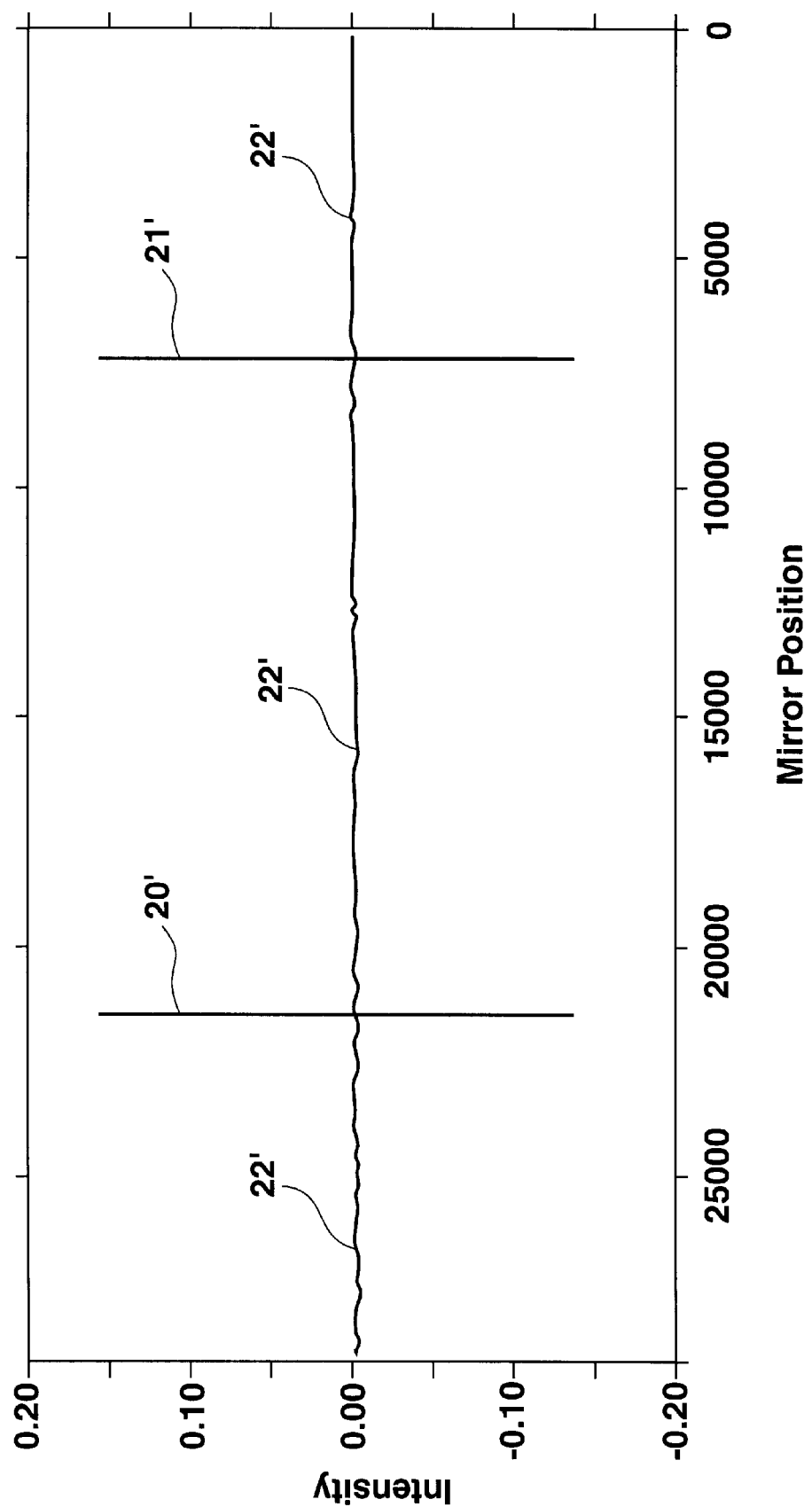
FIG. 3 shows an interferogram having an intermediate level of interference.
Figure 4:
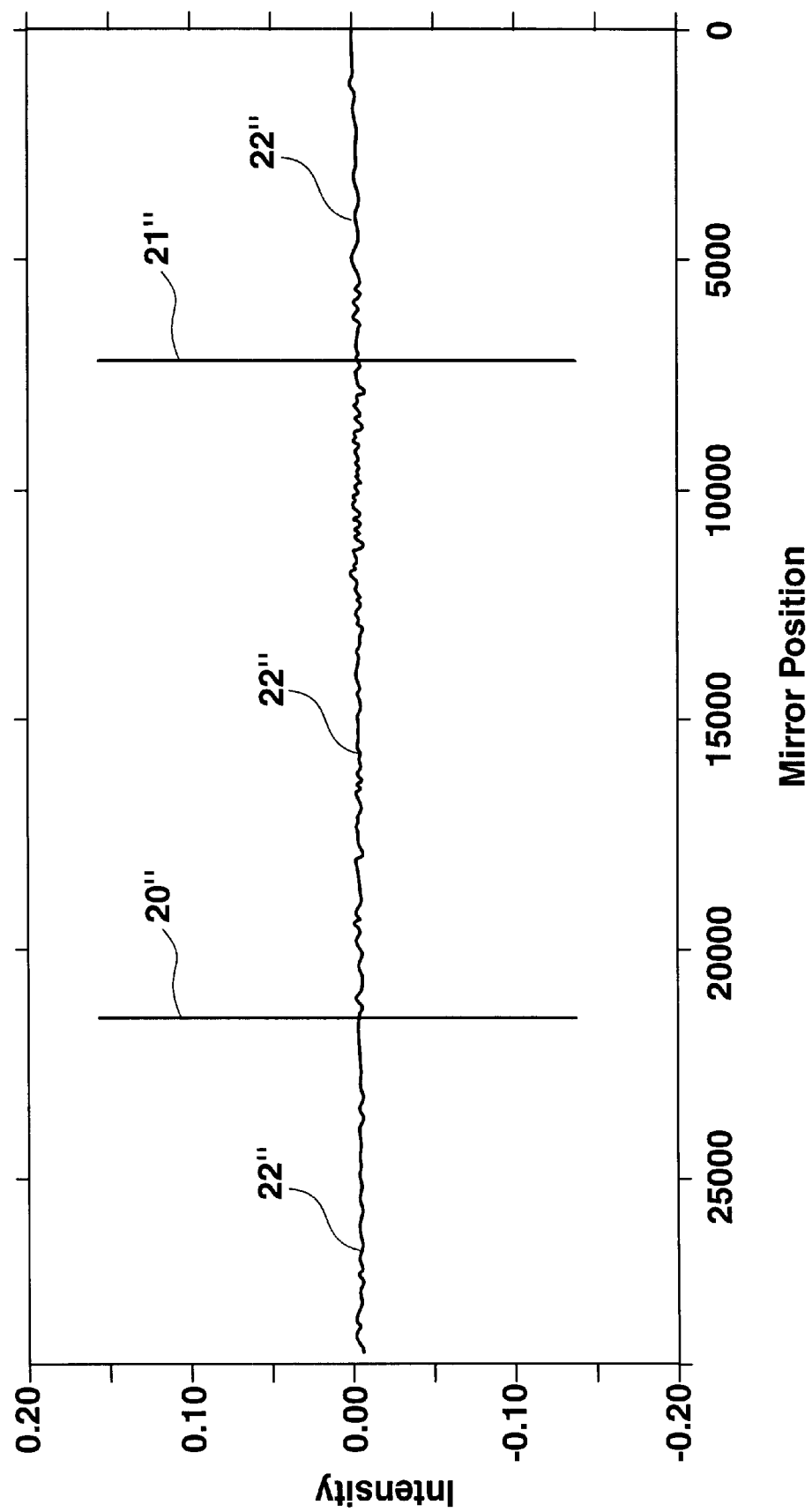
FIG. 4 shows an interferogram having a high degree of interference due to bubble formation.

FIGS. 2, 3 and 4 show examples of interferograms extracted from such chemical composition analysis systems. Two central regions 20, 20', 20" and 21, 21' and 21" are visible in the figures corresponding to the central burst regions of double sided interfergram in which a moveable mirror passes through the spectral region twice, once in a forward moving and once in a backward moving direction. In FIG. 2, the regions 22 outside of the central burst regions 20, 21 are flat and contain essentially no externally introduced intensity fluctuations.

FIG. 3 shows a second example in which the interferogram contains substantial fluctuations visible in intermediate regions 22', external to the central burst regions 20' and 21'. The fluctuations in the intensity regions 22" are substantially due to bubble formation and exhibit characteristic intensity, frequency and time dependencies. This is particularly clear in FIG. 4 in which the intensity regions 22" not occupied by the central bursts 20" and 21" show strong perturbations due to bubble formation. In accordance with the invention, these segments of the interferogram are inspected for characteristic signatures of the intensity fluctuations in order to decide whether or not the data/interferogram is usable.

LIST OF REFERENCE SYMBOLS 1 composition container
2 composition
3 liquid inlet
4 liquid outlet
5 gas inlet
6 Stir member
7 -
8 interferometer means
9 IR beam
10 probe
11 gap
12 interferogram analyzer
13 Fourier transform device
20, 20', 20" central burst region
22, 22', 22" regions showing the perturbations

We claim:
1. A method for determining the spectrum of a chemical composition in a method for the process control of chemical processes using Fourier transform (FT) infrared (IR) spectroscopy, the method comprising the steps of:
   a) feeding a composition into a storage vessel;
   b) stirring said composition;
   c) passing a beam of IR radiation through said composition;
   d) generating an interferogram following step c);
   e) analyzing regions of said interferogram outside a central burst region for unwanted intensity fluctuations;
   f) labeling, following step e), said interferogram as at least one of acceptable and non-acceptable;
   g) repeating steps e)–f) a plurality of times;
   h) adding together acceptable interferograms or segments of interferograms to generate a sum interferogram; and
   i) Fourier transforming said sum interferogram to obtain a spectrum of said composition.

2. The method of claim 1, wherein step e) comprises inspection of at least one of an amplitude, a time, and a frequency dependence of said intensity fluctuations.

3. The method of claim 2, wherein intensity fluctuations in said analyzed regions are added together to generate a sum value.

4. The method of claim 3, wherein step f) comprises the step of comparing said sum value to a maximum allowable positive value.

5. The method of claim 3, wherein step f) comprises the step of comparing said sum value to a maximum allowable negative value.

6. The method of claim 1, further comprising analyzing regions of said central burst, wherein step f) comprises evaluation of said analyzed central burst regions.

7. The method of claim 1, wherein step e) comprises standard commercially available spectroscopy software algorithms.

8. A device for determining the frequency spectrum of a chemical composition used for the process control of chemical processes during Fourier transform (FT) infrared (IR) spectroscopy, the device comprising:

means for feeding a composition into a reaction vessel;

means for stirring said composition;

means for passing a beam of IR radiation through said composition;

means for generating an interferogram of said IR radiation before or after passage through said chemical composition;

means for analyzing segments of said interferogram outside a central burst region for externally introduced, unwanted intensity fluctuations;

means for labeling said interferogram as at least one of acceptable and non-acceptable in dependence on said analyzed intensity fluctuations;

means for adding together accepted interferograms to generate a sum interferogram; and means for Fourier transforming said sum interferogram to obtain a frequency spectrum of said composition.

9. The device of claim 8, wherein said analyzing means comprises means for inspection of at least one of an amplitude, a time, and a frequency dependence of said intensity fluctuations.

10. The device of claim 9, wherein said inspection means comprise means for adding together said intensity fluctuations in said analyzed regions to generate a sum value.

11. The device of claim 10, wherein said labeling means comprise means for comparing said sum value to a maximum allowable positive value.

12. The device of claim 10, wherein said labeling means comprise means for comparing said sum value to a maximum allowable negative value.

13. The device of claim 8, further comprising means for analyzing regions of said central burst, wherein said labeling means comprise means for evaluation of said analyzed central burst region.

14. The device of claim 1, wherein said analyzing means comprise standard commercially available spectroscopy software algorithms.

* * * * *